United States Patent
Scheff

(10) Patent No.: US 6,255,280 B1
(45) Date of Patent: Jul. 3, 2001

(54) PROTECTION AGAINST TRAUMATIC BRAIN INJURY

(75) Inventor: Stephen William Scheff, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 09/288,515

(22) Filed: Apr. 8, 1999

(51) Int. Cl.[7] .............................. A61K 38/00; A61K 9/00
(52) U.S. Cl. .......................... 514/11; 424/400; 424/451; 424/464; 424/489
(58) Field of Search .............................. 514/11; 424/400, 424/464, 474, 489, 452

(56) References Cited

U.S. PATENT DOCUMENTS

| | | |
|---|---|---|
| 4,117,118 | 9/1978 | Harri et al. . |
| 5,162,497 | 11/1992 | Coy et al. . |
| 5,204,327 | 4/1993 | Kiyota et al. . |
| 5,278,143 | 1/1994 | Shepro et al. . |
| 5,292,765 | 3/1994 | Choi et al. . |
| 5,411,952 | 5/1995 | Kaswan . |
| 5,455,279 | 10/1995 | Lipton . |
| 5,466,667 | 11/1995 | Shepro et al. . |
| 5,486,204 | 1/1996 | Clifton . |
| 5,525,590 * | 6/1996 | Bollinger et al. ................ 514/11 |
| 5,573,775 | 11/1996 | Robertson et al. . |
| 5,614,630 * | 3/1997 | Goldin et al. .................. 546/159 |
| 5,639,474 * | 6/1997 | Woo ................................ 424/452 |
| 5,735,772 * | 4/1998 | Schiavoni ........................ 482/11 |
| 5,747,545 | 5/1998 | Lipton . |
| 5,750,646 | 5/1998 | Coy et al. . |
| 5,756,449 | 5/1998 | Andersen et al. . |
| 5,766,629 | 6/1998 | Cho et al. . |
| 5,792,457 | 8/1998 | Tuomanen et al. . |

OTHER PUBLICATIONS

Society for Neuroscience, vol. 24, 1998, abstract No. 675.15.*

Uchino et al, "Amelioration by Cyclosporin A of brain damage in transient forebrain ischemia in the rat", Brain Research, pp 216–226, Aug. 25, 1998.*

Drugs: Factas and Comparison, 1994 edition, pp 2920–2924.*

Shiga et al, "Cyclosporin A pretects against ischemia–repurfusion injury in the brain", Brain Research, pp 145–148, Aug. 4, 1992.*

\* cited by examiner

*Primary Examiner*—Thurman K. Page
*Assistant Examiner*—Amy E Pulliam
(74) *Attorney, Agent, or Firm*—McDermott, Will & Emery

(57) ABSTRACT

The present invention relates to therapeutic uses of cyclosporin A to reduce adverse effects of neural injury.

10 Claims, 4 Drawing Sheets

PROTECTION AGAINST TRAUMATIC BRAIN INJURY

FIELD OF THE INVENTION

The present invention relates to a method for reducing adverse effects of a neural injury by administering to a patient a therapeutically effective amount of cyclosporin A.

BACKGROUND OF THE INVENTION

Severe traumatic brain injuries (TBI) initiate a cascade of events that lead to a plethora of adverse effects including dramatic elevations of intracranial pressure (ICP) and dysfunction of cerebrovascular regulatory mechanisms essential for survival. Ischemic brain injury is observed universally in those patients who die following severe TBI. Intracranial hypertension (IH) following traumatic brain injury is associated with direct effects on cerebral perfusion which may be responsible for secondary ischemia. The contributions of both post-traumatic cerebral edema and alteration in cerebral blood volume to ICP appear to vary based on the length of time after the primary mechanical insult. This combination of vasomotor dysfunction and abnormalities in vascular permeability is characteristic of acute inflammation.

The mortality rate from severe traumatic brain injury (TBI) in the United States alone amounts to 9–30 deaths per 100,000. Those suffering brain injury requiring medical treatment number 160–300 per 100,000, with approximately 20 percent of patients admitted to treatment facilities sustain a moderate to severe degree of injury as measured by the Glasgow Coma Score (GCS) of 3–12. Direct costs of brain injury, including the costs of treatment and long-term care, as well as indirect costs, including disablement and the loss of productivity of brain injury patients and other such costs, are staggering.

One approach to treating severe traumatic brain injuries is with hypothermia, as in U.S. Pat. No. 5,486,204 to Clifton. The procedure includes the introduction of specified medication to reduce the risk of cardiac arrhythmia and a complicated protocol for the treatment which defines time, temperature, rate of change of temperature, the timing of the introduction of medications, and rigidly controlled rewarming to reduce the incidence of rewarming shock in recovering patients.

There exists a need to provide simplified methodology for treating traumatic brain injuries in mammals, including humans. The present invention addresses and solves the problems attendant upon multistep, complicated processes for treating severe traumatic brain injuries.

DISCLOSURE OF THE INVENTION

An object of the present invention is a method of treating a mammal suffering from traumatic brain injury.

Additional objects, advantages and other features of the invention will be set forth in the description which follows and in part will become apparent to those having ordinary skill in the art upon examination of the following or may be learned from the practice of the invention. The objects and advantages of the invention may be realized and obtained as particularly pointed out in the appended claims.

According to the present invention, the foregoing and other objects are achieved in part by a method of treating a mammal, including humans, suffering from traumatic brain injury, which method comprises administering a therapeutically effective amount of cyclosporin A.

Another aspect of the present invention is a pharmaceutical composition for treatment of severe traumatic brain injuries, the composition comprising an amount of cyclosporin A effective for reducing adverse effects of traumatic brain injury and pharmaceutically acceptable carrier.

Additional objects and advantages of the present invention will become readily apparent to those skilled in this art from the following detailed description, wherein embodiments of the invention are described simply by way of illustrating of the best mode contemplated in carrying out the invention. As will be realized, the invention is capable of other and different embodiments, and its several details are capable of modifications in various obvious respects, all without departing from the invention. Accordingly, the drawings and description are to be regarded as illustrative in nature and not as restrictive.

DESCRIPTION OF THE INVENTION

Figure 1:
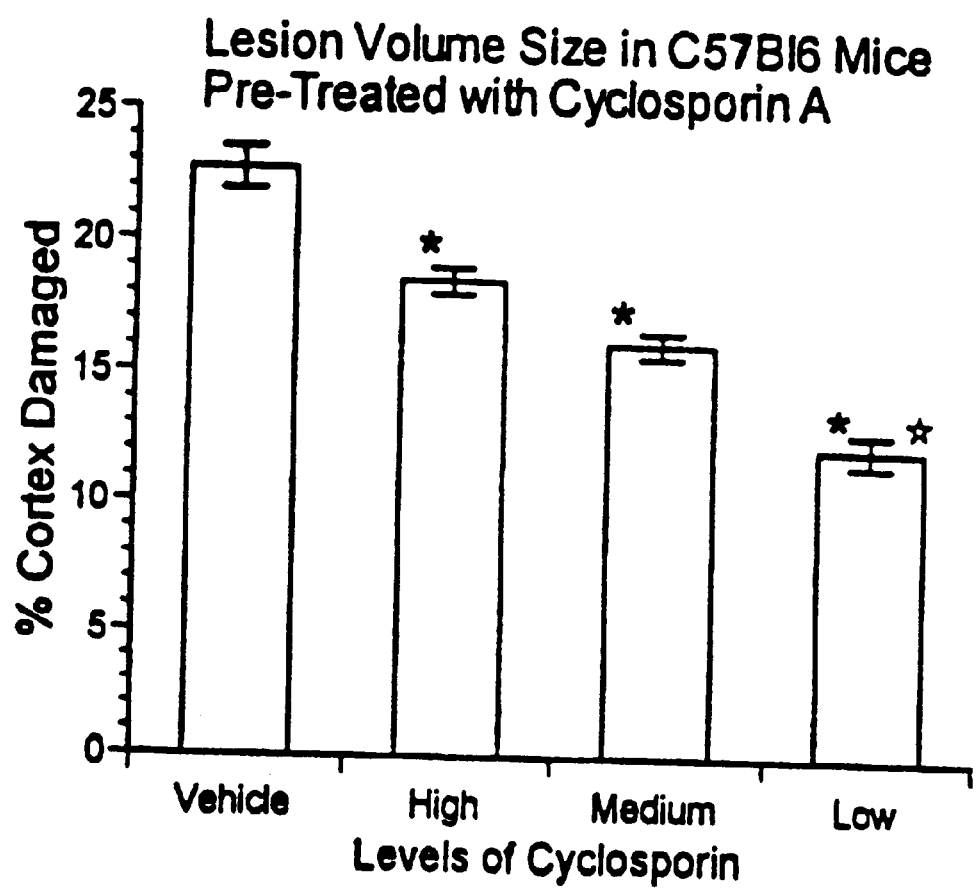
FIG. 1 illustrates the effect of CsA administration before TBI on cortical lesion volume.

The present invention provides a method of treating a mammal, including humans, suffering from traumatic brain injury, which method comprises administering a therapeutically effective amount of cyclosporin A.

Cyclosporin A is known and has been proposed for use for various therapeutic methods. For example, U.S. Pat. Nos. 4,117,118 and 5,766,629, which are incorporated herein in their entirety by reference thereto, describe this compound, methods for preparing this compound, and methods for formulating this compound into pharmaceutical compositions.

The compounds for use in the present invention can be administered as a pharmaceutical composition. The pharmaceutical compositions used in the methods of this invention for administration to animals and humans comprise an active agent in combination with a pharmaceutical carrier or excipient acceptable for delivery of the compounds to the brain.

The pharmaceutical compositions can be in the form of tablets (including lozenges and granules), dragees, capsules, pills, ampoules or suppositories comprising a compound of the invention.

"Pharmaceutical composition" means physically discrete coherent portions suitable for medical administration. "Pharmaceutical composition in dosage unit form" means physically discrete coherent units suitable for medical administration, each containing a daily dose or a multiple (up to four times) or a sub-multiple (down to a fortieth) of a daily dose of the active compound of the invention in association with a carrier and/or enclosed within an envelope. Whether the composition contains a daily dose, or for example, a half, a third or a quarter of a daily dose will depend on whether the pharmaceutical composition is to be administered once or, for example, twice, three times or four times a day, respectively.

Advantageously, the compositions are formulated as dosage units, each unit being adapted to supply a fixed dose of active ingredients. Tablets, coated tablets, capsules, ampoules and suppositories are examples of preferred dosage forms according to the invention. It is only necessary that the active ingredient constitute an effective amount, i.e., such that a suitable effective dosage will be consistent with the dosage form employed in single or multiple unit doses. The exact individual dosages, as well as daily dosages, are determined according to standard medical principles under the direction of a physician or veterinarian.

The active agents can also be administered as suspensions, solutions and emulsions of the active compound in aqueous or non-aqueous diluents, syrups, granulates or powders. Diluents that can be used in pharmaceutical compositions (e.g., granulates) containing the active compound adapted to be formed into tablets, dragees, capsules and pills include the following: (a) fillers and extenders, e.g., starch, sugars, mannitol and silicic acid; (b) binding agents, e.g., carboxymethyl cellulose and other cellulose derivatives, alginates, gelatine and polyvinyl pyrrolidone; (c) moisturizing agents, e.g., glycerol; (d) disintegrating agents, e.g., agar—agar, calcium carbonate and sodium bicarbonate; (e) agents for retarding dissolution, e.g., paraffin; (f) resorption accelerators, e.g., quaternary ammonium compounds; (g) surface active agents, e.g., cetyl alcohol, glycerol monostearate; (h) adsorptive carriers, e.g., kaolin and bentonite; (i) lubricants, e.g., talc, calcium and magnesium stearate and solid polyethylene glycols.

The tablets, dragees, capsules and pills comprising the active agent can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, from polymeric substances or waxes.

The active ingredient can also be made up in microencapsulated form together, with one or several of the above-mentioned diluents.

The diluents to be used in pharmaceutical compositions adapted to be formed into suppositories can, for example, be the usual water-soluble diluents, such as polyethylene glycols and fats (e.g., cocoa oil and high esters, (e.g., $C_{14}$-alcohol with $C_{16}$-fatty acid]) or mixtures of these diluents.

The pharmaceutical compositions which are solutions and emulsions can, for example, contain the customary diluents (with, of course, the above-mentioned exclusion of solvents having a molecular weight below 200, in the presence of a surface-active agent), such as diluents, dissolving agents and emulsifiers. Specific non-limiting examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils (for example, ground nut oil, glycerol, tetrahydrofurfuryl alcohol, polyethylene glycols and fatty acid esters of sorbitol or mixtures thereof.

For parenteral administration, solutions and suspensions should be sterile, e.g., water or arachis oil contained in ampoules and, if appropriate, blood-isotonic.

The pharmaceutical compositions which are suspensions can contain the usual diluents, such as liquid diluents, e.g., water, ethyl alcohol, propylene glycol, surface active agents (e.g., ethoxylated isostearyl alcohols, polyoxyethylene sorbitols and sorbitan esters), polycrystalline cellulose, aluminum methahydroxide, agar—agar and tragacanth, or mixtures thereof.

The pharmaceutical compositions can also contain bulking agents and preservatives, as well as perfumes and flavoring additions (e.g., peppermint oil and eucalyptus oil, and sweetening agents, (e.g., saccharin and aspartame).

The pharmaceutical compositions will generally contain from about 0.0001 to 90 wt. %, preferably about 0.01 to 10 wt. % of the active ingredient by weight of the total composition. In addition to the active agent, the pharmaceutical compositions and medicaments can also contain other pharmaceutically active compounds.

Any diluent in the pharmaceutical compositions of the present invention may be any of those mentioned above in relation to the pharmaceutical compositions. Such compositions may include solvents of molecular weight less than 200 as the sole diluent.

The active compound is administered perorally, parenterally (for example, intramuscularly, intraperitoneally, subcutaneously, transdermally or intravenously), rectally or locally, preferably orally or parenterally, especially perlingually, or intravenously.

The dosage rate, e.g., about 0.0001 to about 200 mg/kg of body weight, such as from about 10 mg/kg to about 150 mg/kg, preferably from about 20 mg/kg to about 40 mg/kg, will be a function of the nature and body weight of the human or animal subject to be treated, the individual reaction of this subject to the treatment, type of formulation in which the active ingredient is administered, the mode in which the administration is carried out and the point in the progress of the disease or interval at which it is to be administered. Thus, it may in some case suffice to use less than a minimum dosage rate, while other cases an upper limit must be exceeded to achieve the desired results. Where larger amounts are administered, it may be advisable to divide these into several individual administrations over the course of the day.

It is presently preferred to administer cyclosporin A parenterally, such as intravenously, in a bolus, so as to obtain the most rapid delivery of the active agent to the brain. A suitable dosage for obtaining attenuation of the effects of traumatic brain injury is from about 1 to about 1000 mg/kg body weight, such as from about 10 to about 100 mg/kg body weight, although the optimum dosage of cyclosporin A will be determined by the physician taking into account the age, weight and general health of the subject. In other embodiments of the present invention, the cyclosporin A may be administered directly to the brain, e.g. intraventricularly, intracerebrally or intracisternally. The dosage may be administered in one or more treatments following traumatic brain injury such as by way of a single or multiple doses or from sustained release compositions over a period of time, such as immediately after the TBI to about 1 or more day after the TBI. Preferably, the initial dosage is administered less than about 6 hours after TBI, such as from about 15 minutes to about 1 hour after injury. However, one or more doses may be administered after 6 hours such as from about 6 hours to about 24–48 hours after injury.

Cyclosporin A may also be administered in association with other therapeutic agents including, for example, antibiotics or antiviral agents.

The following non-limiting examples are given by way of illustration only.

EXAMPLE 1

Pretreatment with Cyclosporin A (CsA) in C57B16 Mice

Adult C57B16 mice were pretreated with a single systemic injection of one of three different doses of CsA (high (150 mg/kg) medium (40 mg/kg) low (20 mg/kg)) 5 min prior to a moderate cortical contusion. Animals also received an additional single systemic injection 24 hr after injury (n=8/group). Control animals received vehicle alone. Animals were killed 7 days post-injury and the brains assessed for changes in lesion volume size utilizing image analysis and stereology. The lesion volume was significantly reduced in all animals injected with CsA as compared to vehicle controls. An ANOVA demonstrated a significant dose effect such that the greatest protection was afforded by animals receiving the lowest dose. The animals treated with 20 mg/kg CsA demonstrated a 45% reduction in lesion volume.

EXAMPLE 2

Pre- vs Post-treatment with Cyclosporin A in ICR Mice

Figure 2:
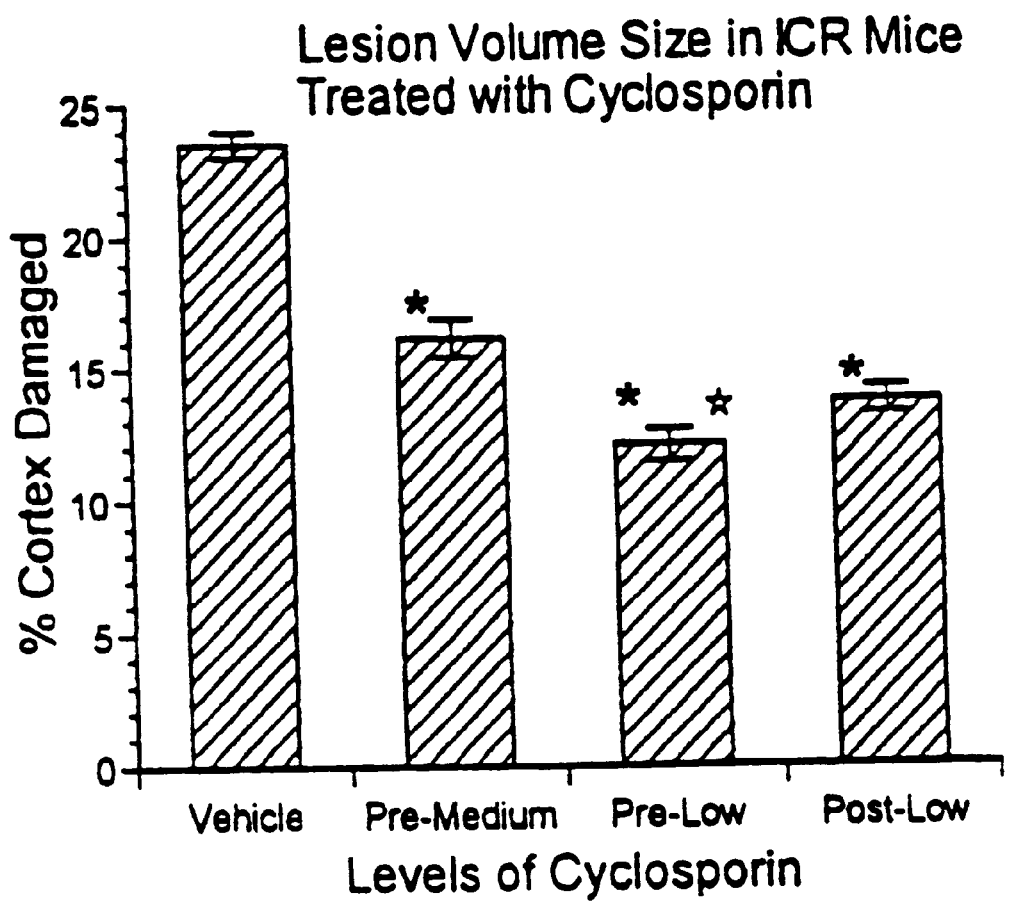
FIG. 2 illustrates the effect of CsA administration pre- and post-injury on cortical lesion volume.

Adult ICR mice were either pre-treated systemically with medium (40 mg/kg) or low (20 mg/kg) doses of CsA 5 min prior to TBI or with a low dose (20 mg/kg) 15 min after TBI. These animals subsequently received an additional injection 24 h later. Control animals received vehicle 5 min prior and 24 h after TBI. Seven days after injury the animals were killed and the brains assessed for possible changes in lesion volume size. All animals receiving CsA showed significant amelioration of lesion volume and animals treated after the injury were equivalent to pre-treated low dose animals. In addition, the effect was observed in an additional strain of mice. The results are shown in FIG. 2.

EXAMPLE 3

Pre- vs Post-treatment with CsA in Rats

Figure 3:
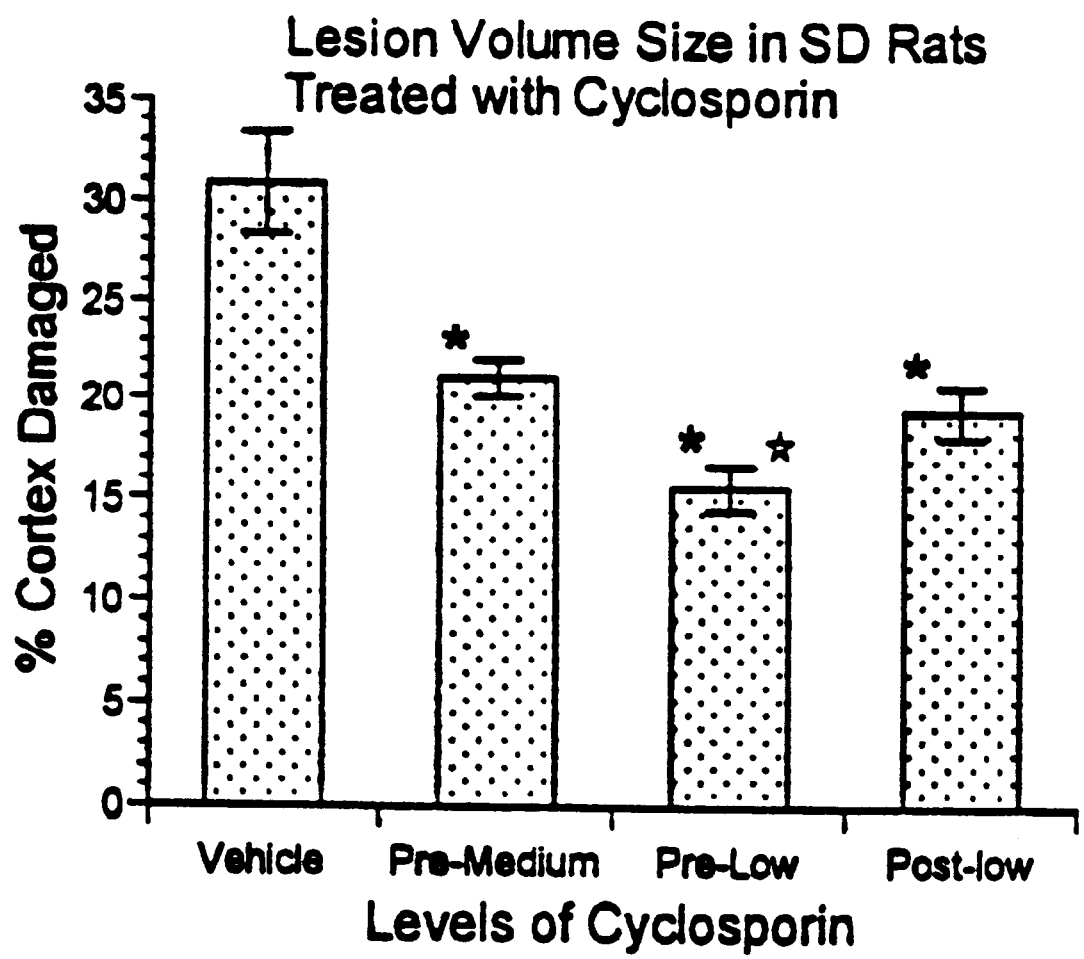
FIG. 3 illustrates the effect of CsA administration pre- and post-injury on cortical lesion volume.

Adult SD rats were either pre-treated systemically with medium (40 mg/kg) or low (20 mg/kg) doses of CsA 5 min prior to TBI or with a low dose (20 mg/kg) 15 min after TBI. These animals subsequently received an additional injection 24 h later. Control animals received vehicle 5 min prior and 24 h after TBI. Seven days after injury the animals were killed and the brains assessed for possible changes in lesion volume size. Identical to that found in the mice, all animals treated with CsA showed significant reductions in the lesion volume size. Post-injury administration of CsA resulted in significant reductions (40%) in lesion volume. The results are shown in FIG. 3.

EXAMPLE 4

Time Course of Initiation of CsA Treatment Following TBI

We administered CsA at a concentration of 20 mg/kg to animals (n=3 adult rats/group) following a moderate level of TBI. The CsA therapy (single systemic injection) was initiated at different time intervals following the injury (15 m, 1 h, 6 h, 24 h). Animals were administered a second injection 24 h after the first injection. All animals survived for 7 days following injury. Brains were assessed for changes in lesion volume size utilizing image analysis and stereological techniques.

Figure 4:
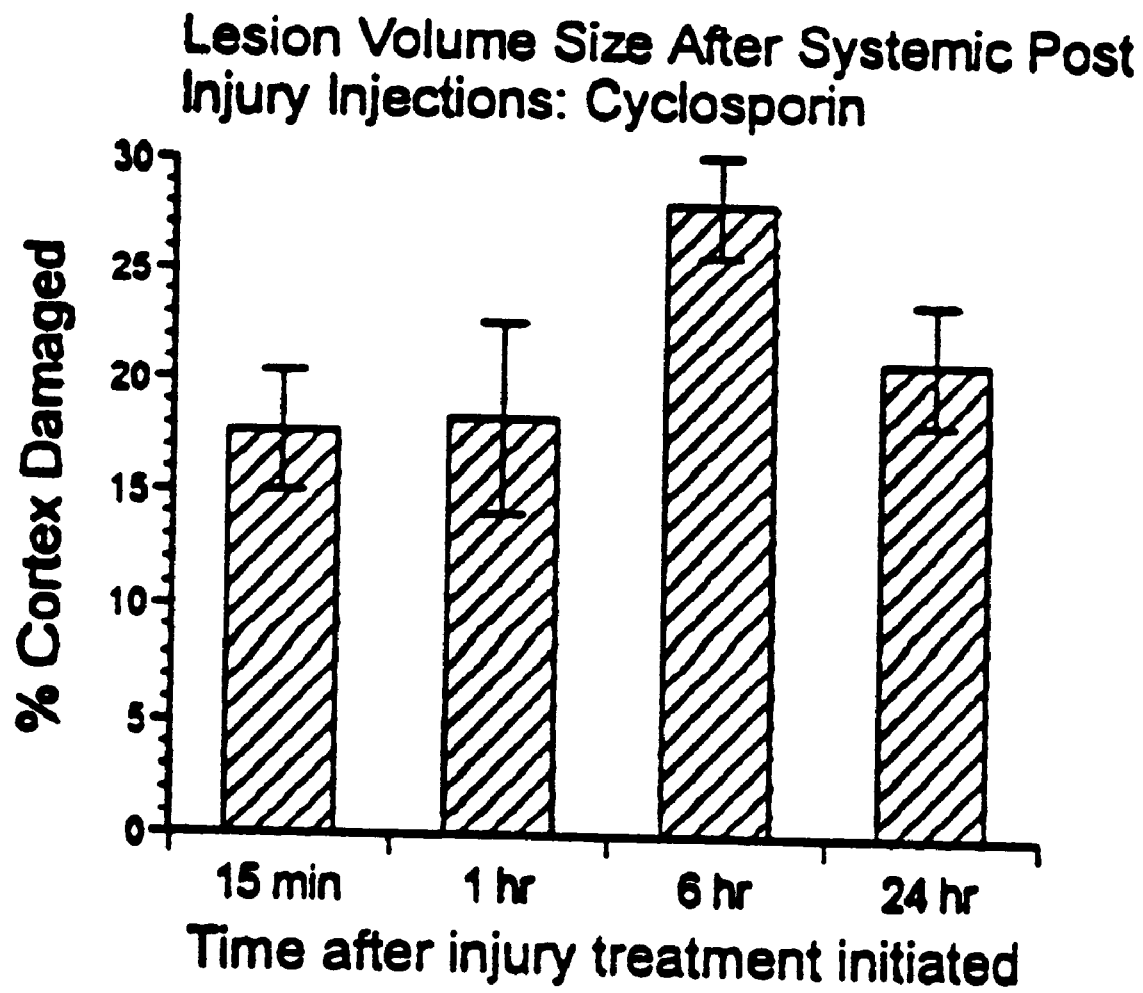
FIG. 4 illustrates the effect of CsA administration after TBI on cortical lesion volume.

The results, as shown in FIG. 4, indicate that the window for therapeutic intervention in this model is at least 1 h and may even be as long as 24 h. The lack of protection at 6 h may relate directly to changes in the blood-brain barrier because in this rodent model of TBI, the BBB is opened immediately following the injury and then closes rapidly (3–6 h post TBI) and reopens around by 24 h.

DETAILED DESCRIPTION OF THE DRAWINGS

FIG. 1.

Cortical lesion volume was significantly reduced in C57B16 mice treated prior to injury with high (150 mg/kg), medium (40 mg/kg), or low (20 mg/kg) with CsA systemically. 7 days following TBI mice were killed and stereological methods used to determine lesion volume size. Values are group means (n=8/group)±SE ★p<0.01 vs vehicle ★p<0.01 vs medium and high.

FIG. 2.

Cortical lesion volume was significantly reduced in ICR mice treated either pre- (medium 40 mg/kg; low 20 mg/kg) or post (20 mg/kg) with CsA systemically. 7 days following TBI mice were killed and stereological methods used to determine lesion volume size. Values are group means (n=8/group)±SE ★p<0.01 vs vehicle ★p<0.01 vs pre-medium.

FIG. 3.

Cortical lesion volume was significantly reduced in SD rats treated either pre- (medium 40 mg/kg/ low 20 mg/kg) or post (20 mg/kg) with CsA systemically. 7 days following TBI rats were killed and stereological methods used to determine lesion volume size. Values are group means (n=10/group)±SE ★p<0.01 vs vehicle ★p<0.01 vs pre-medium.

FIG. 4.

Early initiation of therapy resulted in a significant reduction in cortical lesion volume. This same level of protection of cortical tissue was also observed with the 1 h delay. If treatment was delayed for 6 h there was little or no sparing. however, a delay of 24 h again showed some protection. Bars=group means±SEM (n=3/group).

In the previous descriptions, numerous specific details are set forth, such as specific materials, structures, chemicals, processes, etc., in order to provide a better understanding of the present invention. However, the present invention can be practiced without resorting to the details specifically set forth. In other instances, well-known processing structures have not been described in detail in order not to unnecessarily obscure the present invention.

Only the preferred embodiment of the invention and but a few examples of its versatility are shown and described in the present disclosure. It is to be understood that the present invention is capable of use in various other combinations and environments and is capable of changes or modifications within the scope of the inventive concept as expressed herein.

What is claimed is:

1. A method for treating a mammal suffering from traumatic brain injury caused by an external mechanical force on the cerebral cortex, which method comprises:

administering a therapeutically effective amount of cyclosporin A in a dose from about 1 to about 1000 mg/kg to a mammal in need thereof within about 48 hours after the injury to reduce or ameliorate brain tissue damage by reducing lesion volume size by more than about 5%.

2. The method of claim 1, comprising:

administering the cyclosporin A orally.

3. The method of claim 1, comprising:

reducing lesion volume size by about 10% to about 45%.

4. The method of claim 1, wherein the traumatic injury results from a non-penetrating head wound.

5. The method of claim 1, comprising:
administering the cyclosporin A parenterally.

6. The method of claim 1, comprising:
administering the cyclosporin A to a human in at least one dose within about 24 hours after injury.

7. The method of claim 1, comprising:
administering the cyclosporin A to a human in at least two doses within about 24 hours after injury.

8. The method of claim 1, comprising:
administering the cyclosporin A in a dose from about 10 mg/kg to about 150 mg/kg.

9. The method of claim 1, comprising:
administering the cyclosporin A in a dose from about 20 mg/kg to about 40 mg/kg.

10. The method of claim 1, comprising:
administering the cyclosporin A to a human.

\* \* \* \* \*